(12) United States Patent
Wang et al.

(10) Patent No.: US 9,673,381 B2
(45) Date of Patent: Jun. 6, 2017

(54) LEAD TITANATE COATING AND PREPARING METHOD THEREOF

(71) Applicants: Haidou Wang, Beijing (CN); Zhiguo Xing, Beijing (CN); Binshi Xu, Beijing (CN)

(72) Inventors: Haidou Wang, Beijing (CN); Zhiguo Xing, Beijing (CN); Binshi Xu, Beijing (CN)

( * ) Notice: Subject to any disclaimer, the term of this patent is extended or adjusted under 35 U.S.C. 154(b) by 0 days.

(21) Appl. No.: 14/803,197

(22) Filed: Jul. 20, 2015

(65) Prior Publication Data

US 2016/0027993 A1   Jan. 28, 2016

(30) Foreign Application Priority Data

Jul. 22, 2014   (CN) .......................... 2014 1 0350628

(51) Int. Cl.
*G01L 3/08*   (2006.01)
*H01L 41/187*   (2006.01)
(Continued)

(52) U.S. Cl.
CPC ............ *H01L 41/1875* (2013.01); *C23C 4/06* (2013.01); *C23C 4/134* (2016.01); *C23C 28/021* (2013.01);
(Continued)

(58) Field of Classification Search
CPC ......... B82Y 30/00; G01L 1/16; G01L 5/0019; G01M 5/0033; G01M 99/00;
(Continued)

(56) References Cited

U.S. PATENT DOCUMENTS 3,360,331 A * 12/1967 Manogue ................. B01J 23/14
423/598
4,810,484 A * 3/1989 Uedaira ............... C01G 23/003
423/598
(Continued)

FOREIGN PATENT DOCUMENTS

CN      86105893 A     3/1988
CN     101627484 A     1/2010
(Continued)

OTHER PUBLICATIONS

Gu et al., "Preparation and characterization of PZT coatings sprayed by supersonic plasma spraying," *Materials Science and Engineering of Powder Metallurgy*, 18(4):560-565, 2013. (English abstract).
(Continued)

*Primary Examiner* — Jonathan Dunlap
(74) *Attorney, Agent, or Firm* — Parker Highlander PLLC

(57) ABSTRACT

The invention provides a lead titanate coating and a preparing method thereof. According to the method, mixed powder is sprayed on the surface of a matrix, and through polarization, the lead titanate coating is acquired. The mixed powder comprises $PbTiO_3$ powder, PbO powder and Al powder. Lead titanate ($PbTiO_3$) is a kind of ferroelectric material, and can be used for preparing a piezoelectric sensor. Besides, the PbO powder and the Al powder are added, so that the piezoelectric property of the lead titanate coating can be improved. Since the lead titanate coating prepared by the present invention can be combined with the matrix closely and the intensity of piezoelectric signal is high, it can be widely applied to mechanical parts, such as a piston ring, a cylinder, a gear, and the like, to dynamically monitor the service situations of the parts better.

15 Claims, 9 Drawing Sheets

(51) Int. Cl.

| | | |
|---|---|---|
| *G01L 1/16* | (2006.01) | |
| *H01L 41/08* | (2006.01) | |
| *H01L 41/314* | (2013.01) | |
| *C23C 4/06* | (2016.01) | |
| *C23C 28/02* | (2006.01) | |
| *C23C 4/134* | (2016.01) | |
| *G01M 99/00* | (2011.01) | |
| *G01N 29/24* | (2006.01) | |
| *G01N 27/04* | (2006.01) | |
| *G01L 5/00* | (2006.01) | |
| *G01M 5/00* | (2006.01) | |
| *G01N 3/36* | (2006.01) | |

(52) U.S. Cl.
CPC .............. *C23C 28/027* (2013.01); *G01L 1/16* (2013.01); *H01L 41/0805* (2013.01); *H01L 41/314* (2013.01); *G01L 5/0019* (2013.01); *G01M 5/0033* (2013.01); *G01M 99/00* (2013.01); *G01N 3/36* (2013.01); *G01N 27/041* (2013.01); *G01N 29/24* (2013.01); *G01N 2203/0623* (2013.01)

(58) Field of Classification Search
CPC ............. G01N 27/041; G01N 29/24; G01N 2203/0623; G01N 3/56; C23C 4/067; C23C 4/10; C23C 28/021; C23C 28/027; H01L 41/1875; H01L 41/0805; H01L 41/314
USPC ................. 423/598, 619; 73/776, 862.625; 252/62.9 PZ; 438/3
See application file for complete search history.

(56) References Cited

U.S. PATENT DOCUMENTS

| | | | | |
|---|---|---|---|---|
| 5,294,462 | A * | 3/1994 | Kaiser | C23C 4/131 427/446 |
| 5,449,933 | A | 9/1995 | Shindo et al. | |
| 7,208,324 | B2 * | 4/2007 | Sunahara | B82Y 30/00 257/E21.272 |
| 7,759,847 | B2 * | 7/2010 | Okamura | F02M 51/0603 252/62.9 PZ |
| 8,080,230 | B2 * | 12/2011 | Auer | B82Y 30/00 252/520.2 |
| 9,046,468 | B2 * | 6/2015 | Wang | B82Y 30/00 |
| 2003/0096696 | A1 * | 5/2003 | Nada | C01G 23/002 501/134 |
| 2006/0046320 | A1 * | 3/2006 | Sunahara | B82Y 30/00 438/3 |
| 2009/0060831 | A1 * | 3/2009 | Auer | B82Y 30/00 423/598 |
| 2009/0220765 | A1 * | 9/2009 | Okamura | H01L 41/0471 428/316.6 |
| 2010/0066214 | A1 | 3/2010 | Feltz et al. | |
| 2012/0304778 | A1 | 12/2012 | Nakamura et al. | |
| 2013/0043422 | A1 * | 2/2013 | Shen | C04B 35/491 252/62.9 PZ |
| 2014/0083196 | A1 * | 3/2014 | Wang | B82Y 30/00 73/776 |
| 2014/0374642 | A1 * | 12/2014 | Shen | C04B 35/491 252/62.9 PZ |

FOREIGN PATENT DOCUMENTS

| | | | | |
|---|---|---|---|---|
| CN | 101894843 | A | | 11/2010 |
| CN | 102809451 | A | | 12/2012 |
| CN | 102839345 | A | | 12/2012 |
| CN | 102862339 | A * | 1/2013 | ............... C23C 4/12 |
| CN | 102879289 | A | | 1/2013 |
| CN | 102888579 | A | | 1/2013 |
| EP | 0253512 | A2 * | 1/1988 | ............ C30B 23/00 |
| JP | H05283756 | A | | 10/1993 |
| KR | 10-2009-0124781 | A | | 12/2009 |
| KR | 10-2013-0053786 | A | | 5/2013 |

OTHER PUBLICATIONS

Office Communication issued in Chinese Patent Application No. 201410350024.X, dated Jan. 20, 2016. (English summary of Chinese Office Action).

Office Communication issued in Chinese Patent Application No. 201410350627.X, dated Feb. 3, 2016. (English summary of Chinese Office Action).

Office Communication issued in Chinese Patent Application No. 201410350628.4, dated Jan. 26, 2016. (English summary of Chinese Office Action).

Office Communication issued in Chinese Patent Application No. 201410350033.9, dated Nov. 23, 2015. (English translation of Chinese Office Action).

Office Communication issued in Chinese Patent Application No. 201410350620.8, dated Jan. 20, 2016. (English summary of Chinese Office Action).

Zuo et al., "Experimental Study on Piezoelectricity of PZT Coatings by Plasma Spraying" *China Mechanical Engineering,* 11(4):435-438, 2000. (English abstract).

* cited by examiner

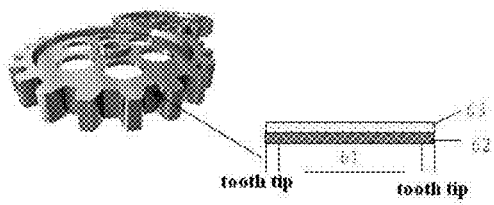 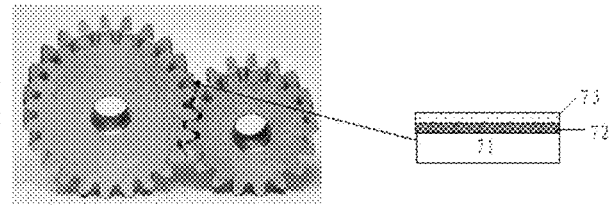
Figure 6          Figure 7
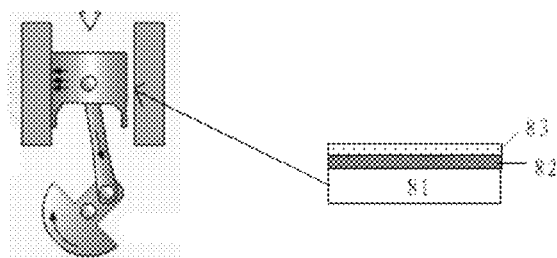 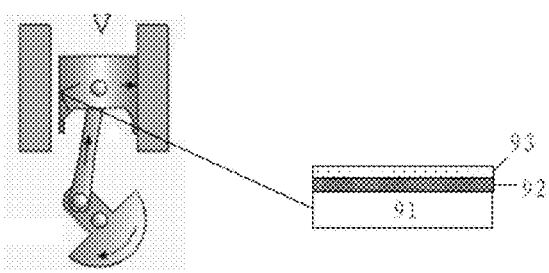
Figure 8          Figure 9
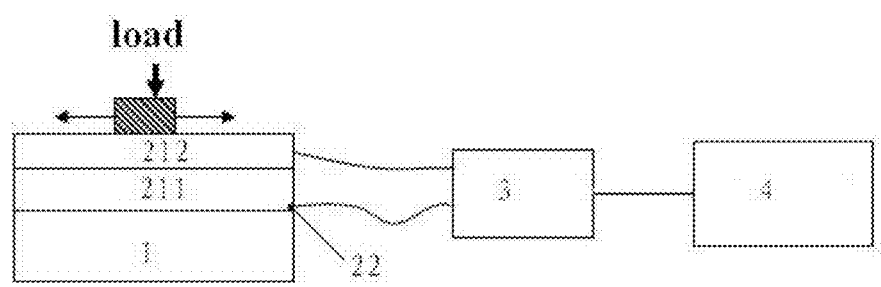
Figure 10

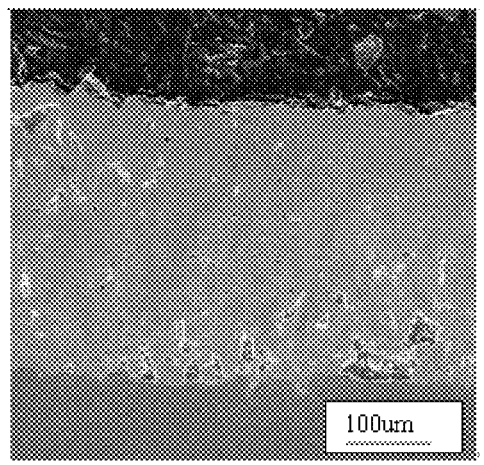
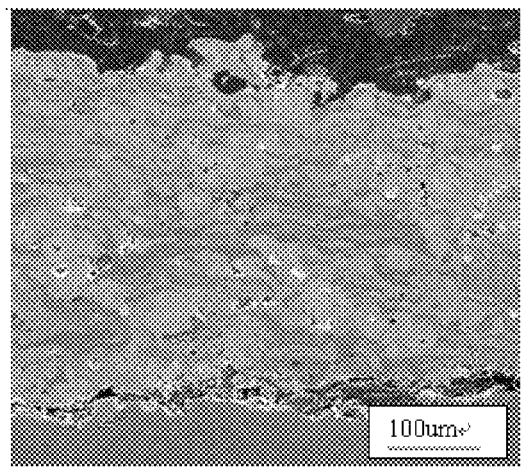
Figure 14                                                    Figure 15
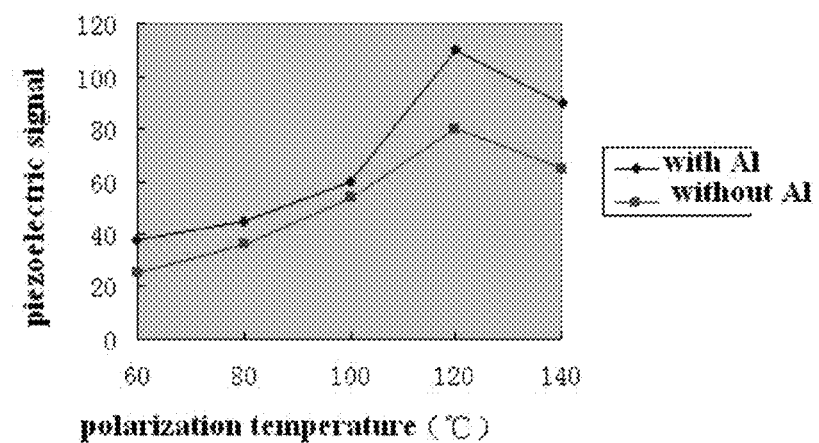
Figure 16

LEAD TITANATE COATING AND PREPARING METHOD THEREOF

This application claims the benefit of priority to Chinese Patent Application No. 201410350628.4, filed Jul. 22, 2014. The entire content of the above-referenced disclosure is specifically incorporated herein by reference.

FIELD OF THE INVENTION

The present invention relates to the field of piezoelectric material, and particularly to a lead titanate coating and preparing method thereof.

BACKGROUND OF THE INVENTION

In order to improve the wearability of some mechanical parts, such as gear, piston and cylinder, a wear-resistant coating is commonly arranged on the surface of these parts. During long-term service of these parts, however, the naturally occurring grown-in micro-defects thereof still will accumulate slowly, and may interact with post micro-damages, so that fatal damage will occur since quantitative change finally leads to qualitative change. If one definite signal can be obtained before the damage of the parts due to qualitative change appears, or the process of quantitative change accumulation for micro-damages of parts can be precisely mastered, accidents can be avoided as much as possible.

At present, fatigue wear tests on part surface mostly take variation of the factors such as vibration, frictional coefficient, and temperature as a judging basis for evaluating abrasion state of part surfaces. When the actual value of the selected judging factors exceeds a pre-determined threshold value, it indicates failure of the part surface. Afterwards, the failed part is subjected to fracture analysis to reversely infer the mechanism of failure by experience or classical theory. However, such failure behavior and mechanism study mainly characterized by "ex-post judgment" cannot estimate critical failure state of the part surfaces. Hence, a controlling mechanism capable of dynamically monitoring and controlling failure of part surface is impossible to be established.

At present, on-line monitoring of the damage on the part surface mainly relies on the piezoelectric sensor arranged for collecting information on the working status of the parts, so that the variation in the service state of the surface coating can be monitored by sorting and analyzing the signal exported from the sensor. Among these, the piezoelectric sensor is prepared according to the piezoelectric effect of existing piezoelectric materials such as barium titanate and lead titanate, which is required to be disposed around the coating in service or bonded to the mechanical equipments or parts during application.

However, there are problems, such as weak strength or distortion of the damage information on the surface coating of the part, when the prior art piezoelectric sensors are used to dynamically monitor the damage situations of the coating in service on the part surface.

SUMMARY OF THE INVENTION

In order to address the problems mentioned above, the present invention provides a lead titanate coating and a preparing method thereof. The lead titanate coating provided according to the present invention possesses more excellent piezoelectric properties, and can be combined with a matrix closely, which can further increases the information intensity for dynamically monitoring surface damage of the parts, and is favorable for applications.

The present invention provides a lead titanate coating, which is prepared by spraying a mixed powder on a surface of a matrix and then subjecting it to polarization, wherein the mixed powder comprises $PbTiO_3$ powder, PbO powder and Al powder.

Preferably, the mass ratio among the $PbTiO_3$ powder, the PbO powder and the Al powder is (5-8):(1-2):(1-3).

Preferably, the particle size of the $PbTiO_3$ powder is in the range from 40 μm to 60 μm.

Preferably, the particle size of the PbO powder is in the range from 40 μm to 70 μm.

Preferably, the particle size of the Al powder is in the range from 30 μm to 40 μm.

Preferably, the thickness of the lead titanate coating is in the range from 45 μm to 55 μm.

Preferably, the lead titanate coating further comprises a wear-resistant layer.

Preferably, the lead titanate coating further comprises a priming layer.

The present invention provides a method for preparing a lead titanate coating, which comprises the following steps:

spraying a mixed powder on a surface of a matrix, and subjecting it to polarization, to produce the lead titanate coating, wherein the mixed powder comprises $PbTiO_3$ powder, PbO powder and Al powder.

Preferably, the spraying is supersonic plasma spraying.

As compared to the prior art, a lead titanate coating according to the present invention is obtained by spraying a mixed powder comprising $PbTiO_3$ powder, PbO powder and Al powder on the surface of a matrix and subjecting it to polarization. Lead titanate ($PbTiO_3$) is a kind of ferroelectric material, which can be used for preparing a piezoelectric sensor. During the formation of the coating layer, the following reaction will occur: $PbTiO_3 \rightarrow PbO + TiO_2$. In the present invention, PbO powder is added for purpose of supplementing the lead lost due to volatilization, so that the above reaction may proceed to the left side as far as possible. In addition, since PbO tends to decompose and volatilize at a high temperature of 880° C. or above, Al powder, which can encapsulate both $PbTiO_3$ powder and PbO powder, is also added in the present invention, so that the piezoelectric property of the lead titanate coating can be improved by the present invention. The lead titanate coating prepared according to the present invention can be combined with the matrix closely and exhibit a high piezoelectric signal intensity. Therefore, the lead titanate coating can be widely applied to mechanical parts, such as a piston ring, a cylinder, a gear, and the like, to dynamically monitor the service situations of the parts better.

BRIEF DESCRIPTION OF THE FIGURES

FIG. 6 is a schematic diagram showing a gear provided by an embodiment of the present invention;

FIG. 7 is a schematic diagram showing a gear provided by another embodiment of the present invention;

FIG. 8 is a schematic diagram showing a cylinder and piston assembly provided by an embodiment of the present invention;

FIG. 9 is a schematic diagram showing a cylinder and piston assembly provided by another embodiment of the present invention;

FIG. 10 is a schematic diagram showing the process of abrasion test of a sensing system provided by an embodiment of the present invention;

FIG. 14 shows the cross-sectional morphology of the coating provided by Example 1 of the present invention;

FIG. 15 shows the cross-sectional morphology of the coating provided by Comparative Example 1 of the present invention;

FIG. 16 is a graph showing the piezoelectric signal of the coatings provided by Examples 7-11 of the present invention and Comparative Examples 7-11 as a function of the polarization temperature;

DETAILED DESCRIPTION OF THE INVENTION

Figure 1:
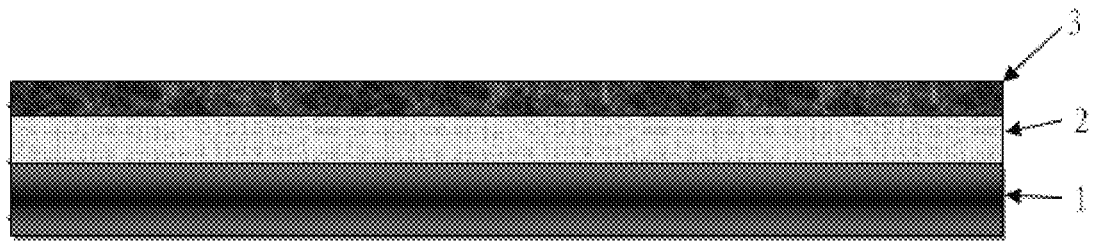
FIG. 1 is a schematic diagram showing a composite coating provided in an embodiment according to the present invention.

In order to further understand the present invention, preferred embodiments of the invention are described with reference to Examples, but it should be understood that these descriptions are only intended to further illustrate the characteristics and advantages of the present invention without limiting the claims of the invention.

The present invention provides a lead titanate coating, which is prepared by spraying a mixed powder on a surface of a matrix and then subjecting it to polarization, wherein the mixed powder comprises $PbTiO_3$ powder, PbO powder and Al powder.

The lead titanate coating provided by the present invention possesses more excellent piezoelectric properties, and can be combined with a matrix closely, thereby can be better applied to dynamically monitor the service situations of the parts as a piezoelectric coating.

The mixed powder for forming the lead titanate coating of the invention comprises $PbTiO_3$ powder. Lead titanate ($PbTiO_3$) is a kind of ferroelectric material, and can be used for preparing piezoelectric sensors. The $PbTiO_3$ powder is a lead titanate powder having a tetragonal phase, wherein the particle size is preferably in the range from 40 µm to 60 µm, and more preferably in the range from 45 µm to 55 µm. When the lead titanate powder with a particle size less than 40 µm is used, severe burning will occur, whereas when the particle size is more than 60 µm, some unmelted particles will be present, both of which will influence the performance of the coating. Furthermore, if the particle size of the sprayed $PbTiO_3$ powder is too large, the particles have poor flowability and also tend to block the nozzle, resulting in poor spraying. The shape of the $PbTiO_3$ powder can be spherical, oval or an irregular shape, and preferably the shape is spherical.

In the present invention, the mixed powder comprises PbO powder. Preferably, the particle size of the PbO powder is controlled to be in the range from 40 µm to 70 µm, and more preferably in the range from 50 µm to 60 µm. The shape of the PbO powder can be spherical, oval or an irregular shape, and preferably the shape is spherical.

During formation of the coating, the following reaction may occur: $PbTiO_3 \rightarrow PbO+TiO_2$.

In the present invention, PbO powder is added for the purpose of supplementing the lead lost due to volatilization, so that the above reaction may proceed to the left side as far as possible and to reduce side reactions as far as possible, thereby the coating performance will be ensured.

In the present invention, the mixed powder further comprises Al powder. The particle size of the Al powder (aluminum powder) is preferably in the range from 30 µm to 40 µm, and more preferably in the range from 33 µm to 38 µm. The shape of the aluminum powder can be spherical, oval or an irregular shape, and preferably the shape is spherical.

Since PbO tends to decompose and volatilize at a high temperature of 880° C. or above, Al powder, which can encapsulate both $PbTiO_3$ powder and PbO powder, is also added in the present invention, so that the piezoelectric property of the lead titanate coating can be improved by the present invention. The lead titanate coating prepared by the present invention can be combined with the matrix closely, and exhibit a high piezoelectric signal intensity. Therefore, the lead titanate coating can be widely applied to mechanical parts, such as a piston ring, a cylinder, a gear, and the like, to dynamically monitor the service situations of the parts better.

Furthermore, respective proportions of the $PbTiO_3$ powder, the PbO powder and the Al powder have their corresponding optimal effects. If the amount of the $PbTiO_3$ powder is too high, it easily leads to heavy volatilization of Pb, whereas if the amount of the $PbTiO_3$ powder is too low, it will lead to poor performance of the coating layer and the piezoelectric coating will be not dense. As to the Al powder, an excessive amount thereof will result in poor or even very weak signal of the piezoelectric coating, whereas if the amount thereof is too low, the binding action will be not strong, so that less piezoelectric sprayed powder can be encapsulated, leading to a poor spraying effect. In addition, excessive PbO powder may result in more impurities in the coating, whereas less PbO powder will cause the above reaction to proceed to the right side more easily since more $PbTiO_3$ decomposes, and also result in poor spraying effect. Preferably, the mass ratio among the $PbTiO_3$ powder, the PbO powder and the Al powder is (5-8):(1-2):(1-3), and for example, the above mass ratio of these 3 components can be 8:1:1, 7:1:2, and 5:2:3, and more preferably 7:1:2, so as to achieve an optimal effect.

In the present invention, the thickness of the lead titanate coating is preferably in the range from 45 μm to 100 μm, and more preferably in the range from 50 μm to 60 μm. Excessively thin coating may result in inaccurate monitoring, while excessively thick piezoelectric coating will lead to unstable electrical signal, since transmission efficiency of the electric charge in the coating can be weaken due to a great amount of pores and crackles inside the excessively thick coating. In addition, since more pores and crackles are easily to be formed if the coating is too thick, the quality of the coating may be influenced, resulting in early failure of the coating. Additionally, it may bring about certain troubles during spraying if the coating is too thick.

Preferably, the lead titanate coating further comprises a wear-resistant layer, so that a composite coating having both wearing and fatigue resistance and piezoelectric sensing performance can be formed. The wear-resistant layer is a surface layer, which not only can be used as an "armour" to protect from contacting with the stress outside and to exert a protection action, but also as an electrode and a conductor for signal output.

The material for preparing the wear-resistant layer is preferably the Fe—Cr—B—Si alloy, i.e., forming an iron-chromium-boron-silicon coating. Since the Fe—Cr—B—Si alloy is cheap in price, can be well bonded to $PbTiO_3$, and has good wearability, the Fe—Cr—B—Si alloy is preferably used as the material for preparing the wear-resistant layer. This can further increase the wearability of the surface of the parts. The thickness of the wear-resistant layer is preferably from 50 μm to 100 μm, and more preferably, from 60 μm to 80 μm. The particle size of the powder for the wear-resistant layer is preferably from 40 μm to 70 μm, and more preferably from 50 μm to 60 μm.

A composite coating provided by an example of the present invention is shown in FIG. 1, which is a schematic diagram showing a composite coating provided by an example of the present invention. In FIG. 1, the numeral 1 represents a matrix, the numeral 2 represents a piezoelectric coating, and the numeral 3 represents a wear-resistant layer. In this example, the lead titanate coating comprises: a piezoelectric coating 2 covering a surface of matrix 1; and a wear-resistant layer 3 covering the piezoelectric coating 2. The lead titanate coating has excellent performances, which is a smart and wear-resistant sensing composite coating.

Preferably, the lead titanate coating further comprises a priming layer. The priming layer is arranged between the piezoelectric coating and the matrix, which has a very strong binding degree with both the $PbTiO_3$ and the matrix. The material for preparing the priming layer is preferably NiAl alloy or NiCr alloy, and more preferably is NiAl alloy. The particle size of the powder for the priming layer is preferably from 30 μm to 50 μm, and more preferably, from 35 μm to 45 μm. The thickness of the priming layer is preferably from 15 μm to 25 μm.

It should be noted that, the source of each powder is not particularly limited, and the powder can be obtained by granulation, or can be purchased from the market.

The invention also provides a method for preparing a lead titanate coating, which comprises the following steps:
spraying a mixed powder on a surface of a matrix, and subjecting it to polarization, to produce the lead titanate coating, wherein the mixed powder comprises $PbTiO_3$ powder, PbO powder and Al powder.

In the present invention, the matrix is preferably a metallic matrix, and more preferably is s matrix of 45# steel. That is, the matrix can be a moving parts of a steam turbine, a compressor, and a pump, and also can be parts, such as gear, shaft and piston pin etc. (the parts should be subjected to high-frequency quenching, or flame surface quenching), or can be a cast. Alternatively, the matrix is a copper matrix or an aluminum matrix, so as to be suitable for parts for other applications.

Preferably, before spraying the surface of the matrix, the present invention further comprises subjecting the matrix to a quenching treatment to increase its hardness, wherein the hardness will generally reach to about HRC55.

Preferably, before spraying the surface of the matrix, the present invention further comprises performing a pretreatment on the matrix to obtain a coarse surface of the matrix, which facilitates to improve the binding degree between the matrix and the coating.

Particularly, the pretreatment comprises: the surface of the matrix is treated by an abrasive blasting process, wherein the brown corundum is preferably used as the sand material in the abrasive blasting process; the particle size of the brown corundum is preferably from 15-mesh to 30-mesh, and more preferably, from 16-mesh to 24-mesh; the air pressure for abrasive blasting is preferably from 0.5 MPa to 1 MPa, and more preferably from 0.6 MPa to 0.8 MPa; the angle for abrasive blasting is from 30° to 60°, and more preferably is 45°; and the distance for abrasive blasting is preferably from 130 mm to 160 mm, and more preferably is 145 mm.

Preferably, before spraying the surface of the matrix, the present invention further comprises performing a heat treatment on the matrix, which brings the temperature of the matrix to 120° C.

On the pre-treated surface of the matrix, a mixed powder is firstly sprayed to form a coating thereon in an embodiment of the present invention.

In the present invention, the mixed powder comprises the $PbTiO_3$ powder, the PbO powder and the Al powder. Each material is described as above, and will not be further illustrated below.

In the present invention, the piezoelectric coating is prepared by spraying the mixed powder. The adhesion process required in conventional applications can be avoided by the piezoelectric component prepared in this manner, so that the disadvantages resulted from adhesion, such as strain transmission loss, failure of a binder and poor adhesive performance can be avoided, which improves the reliability of the piezoelectric ceramic arrays.

In the present invention, the spraying can be flame spraying, plasma spraying and supersonic plasma spraying etc., and preferably is supersonic plasma spraying.

The supersonic plasma spraying described herein comprises the following steps: heating a powder to a molten state in a plasma flame jet at a relatively high temperature, and spraying it onto a surface of a part at a high speed. Once striking the surface of the part, the spherical powder in the molten state will produce plastic deformation to adhere to the surface of the part. Also, powders will combine to each other based on the plastic deformation. With increased spraying duration, a coating with a certain thickness is thus obtained on the surface of the part.

The piezoelectric coating prepared by supersonic plasma spraying process has a series of advantages: firstly, the thickness of the coating can be controlled below tens of micrometers by supersonic plasma spraying, so that the thickness of the piezoelectric coating prepared plus the electrode and the leading-out wire can be controlled to be 100 μm or less, which makes it possible to use a piezoelectric ceramic component in the applications with special requirements for the thickness of the component, such as a coating. This advantage can not be achieved by the piezoelectric components prepared by a sintering process. Secondly, supersonic plasma spraying has high production efficiency for large area spraying. As a result, use of such spraying technology exhibits very significant advantages during preparation of piezoelectric ceramic component arrays with large area.

Additionally, there are problems in the spaying coating, such as high porosity, inclusion of impurities and loss of components, as well as low binding strength with the matrix or the like, which have a great influence on the performance and use of the piezoelectric coating. The porosity of the coatings obtained by conventional plasma spraying is greater than 3%, while for supersonic plasma spraying, the porosity is usually lower than 2%, and it can be further adjusted and reduced by optimization of process parameters, such as spraying power, flow rate of working gas, particle size of the powder, and the like. Consequently, the piezoelectric coating prepared by supersonic plasma spraying not only can be combined with the matrix closely, but also has advantages, such as low porosity, excellent binding properties, low surface roughness obtained easily by grinding and finishing, and more importantly, more excellent piezoelectric properties.

In the present invention, the spraying voltage for the supersonic plasma spraying is preferably from 110 V to 130 V, and more preferably is 120 V; the spraying current is preferably from 430 A to 450 A, and more preferably is 440 A; the spraying power is preferably from 45 kW to 65 kW, and more preferably is from 50 kW to 60 kW; and the spraying distance is preferably from 90 mm to 110 mm, and more preferably is 100 mm.

After completion of the spraying, the resulting coating is placed in a polarization field for polarization in an embodiment of the present invention, and the lead titanate coating with excellent piezoelectric property is obtained after standing.

Figure 2:
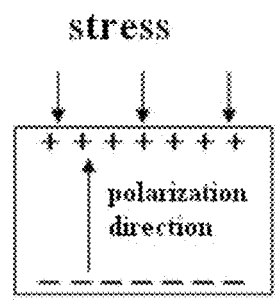
FIG. 2 is a schematic diagram showing a direct piezoelectric effect.
Figure 3:
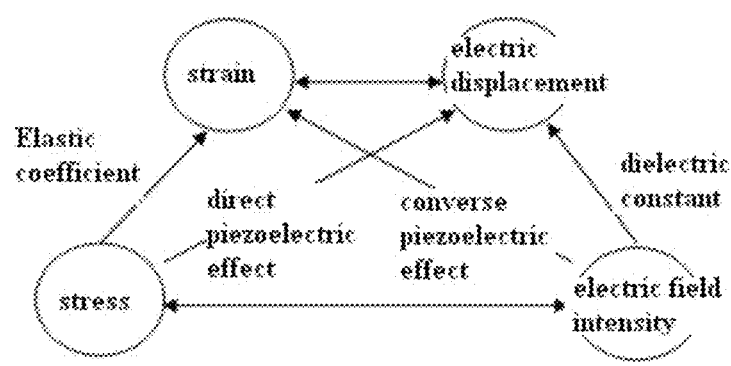
FIG. 3 is a schematic diagram showing conversion of energy.

Piezoelectric effect occurs during polarization, with conversion of energy accompanied. The direct piezoelectric effect is shown in FIG. 2, which is a schematic diagram of direct piezoelectric effect. If the polarization direction is wrong, the polarization effect will be influenced. The conversion of energy is shown in FIG. 3, which is a schematic diagram of energy conversion.

In the present invention, the polarization temperature is preferably from 60° C. to 160° C., and more preferably is from 80° C. to 140° C., and most preferably, is 120° C. The polarization duration is preferably from 20 min to 40 min, and more preferably is 20 min. If the duration is too short, the lead titanate coating can not be fully polarized. However, if the duration is too long, breakdown may occur to the coating, thereby the monitoring function could not be achieved.

In an embodiment of the present invention, the matrix with the lead titanate coating is placed in a silicone oil bath, and a voltage is applied for polarization. In the present invention, the intensity of the polarization field is preferably from 2.4 KV/mm to 2.6 KV/mm. After polarization and standing, the lead titanate coating is obtained. The standing duration is preferably from 24 h to 48 h, and more preferably is 40 h.

Figure 4:
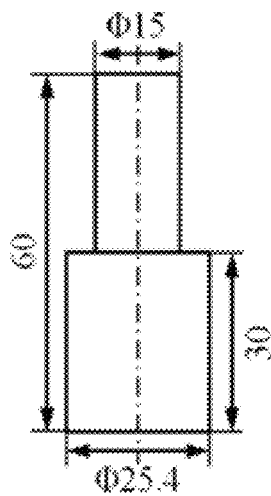
FIG. 4 is a graph showing a sprayed sample for testing the binding strength of a coating according to the invention.
Figure 5:
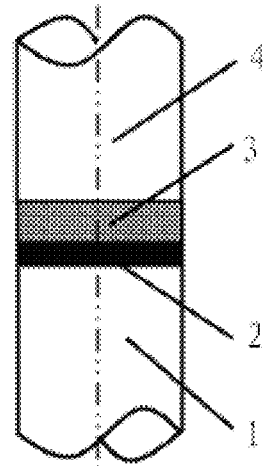
FIG. 5 is a graph showing a stretched sample for testing the binding strength of a coating according to the invention.

After the lead titanate coating is obtained, its piezoelectric property or piezoelectric signal, or the like is tested in the present invention. The piezoelectric signal of the lead titanate coating was measured by ZJ-4AN quasi-static piezoelectric constant meter. The cross section of the lead titanate coating was observed using Nova NanoSEM450 Scanning Electron Microscope. The porosity of the coating was measured using a gray scale method, which specifically comprised the following steps: the metallographic SEM morphology of the cross section of the coating was stretched and enhanced by a gray scale method, so that the pore will emerge due to dark background; and the ratio of the pore area to the total area of the cross section was then calculated by an image processing software, which was recorded as the porosity of the coating. The microhardness of the coating was tested using Micromet 6040 Automatic Loading Switch Microhardness Tester under the following conditions: the loading tested of 25 g, the loading time of 15 s, and loading direction perpendicular to the coating. The microhardness was expressed as the average value of multiple measurements. The samples were prepared according to national standard GB9796-88 "Testing methods of aluminum and its alloys coatings produced by thermal spraying". Subsequently, the binding strength between the coating and the matrix was measured using coupled part stretching method by an MTS universal testing machine. At each test level, the average value of the binding strength from 6 tests was collected as the binding strength value of the coating at this test level. Among those, the sprayed sample is shown in FIG. 4, which is a graph showing the sprayed sample for testing the binding strength of a coating according to the invention. The stretched sample after bonding is shown in FIG. 5, which is a graph showing the stretched sample for testing the binding strength of a coating according to the invention. In FIG. 5, the numeral 1 represents a coupled part, the numeral 2 represents a bonding coating, the numeral 3 is a lead titanate coating (spraying layer), and the numeral 4 is a matrix sample (Spraying sample). Specific test method includes: abrasive blasting is firstly performed on the coupled part, and subsequently, center-to-center bonding is carried out between the coupled part and the sprayed part according to the present invention, wherein the material for bonding is E-7 high-strength glue. After bonding, the bonded part is dried at a drying temperature of 100° C. in an oven for 4 h. After complete curing, the sample is subjected to a tension test, and the critical load is recorded at the time of tensile failure of the sample. Finally, the binding strength is calculated by dividing the critical load by the bonding area between the sample and the coating.

The result indicates that the lead titanate coating has more excellent piezoelectric property, and is able to be combined with a matrix closely, which facilitates its application in dynamical monitoring of the surface damage of parts.

Preferably, prior to formation of the piezoelectric coating, the present invention further comprises formation of a priming layer by spraying the surface of the matrix, followed by spraying the surface of the priming layer and subjecting it to polarization, in order to form a piezoelectric coating.

That is, preferably, the lead titanate coating further comprises a priming layer. The priming layer is arranged between the piezoelectric coating and the matrix, wherein the priming layer is well combined with the PbTiO$_3$ and the matrix.

The material for preparing the priming layer is preferably NiAl alloy or NiCr alloy, and more preferably is NiAl alloy. The particle size of the powder for the priming layer is preferably from 30 μm to 50 μm, and more preferably, from 35 μm to 45 μm; and the thickness of the priming layer is from 15 μm to 25 μm.

In an embodiment of the present invention, the priming layer is preferably formed by supersonic plasma spraying under specific process conditions comprising: a spraying voltage of 110V to 130V, preferably, 120V; a spraying current of 370 A to 400 A, preferably, 385 A; a spraying power of 30 kW to 50 kW, preferably, 40 kW; and a spraying distance of 100 mm to 120 mm, preferably, 110 mm.

Preferably, prior to polarization, the present invention further comprises formation of a wear-resistant layer by spraying the coating followed by polarization, to give the lead titanate coating.

That is, preferably, the lead titanate coating further comprises a wear-resistant layer, so that a composite coating having both wearing and fatigue resistance and piezoelectric sensing function can be formed. The wear-resistant layer is a surface coating, which not only can be used as an "armour" to protect from contacting with the stress outside and to exert a protection action, but also as an electrode and a conductor for signal output.

The material for preparing the wear-resistant layer is preferably the Fe—Cr—B—Si alloy, i.e., forming an iron-chromium-boron-silicon coating. Since the Fe—Cr—B—Si alloy is cheap in price, can be well bonded to PbTiO$_3$, and has good wearability, the Fe—Cr—B—Si alloy is preferably used as the material for preparing the wear-resistant layer. This can further increase the wearability of the surface of the parts. The thickness of the wear-resistant layer is preferably from 50 μm to 100 μm, and more preferably, from 60 μm to 80 μm. The particle size of the powder for the wear-resistant layer is preferably from 40 μm to 70 μm, and more preferably from 50 μm to 60 μm.

In an embodiment of the present invention, the wear-resistant layer is preferably formed by supersonic plasma spraying under specific process conditions comprising: a spraying voltage of 110V to 130V, preferably, 120V; a spraying current of 410 A to 430 A, preferably, 420 A; a spraying power of 35 kW to 55 kW, preferably, 45 kW; and a spraying distance of 90 mm to 100 mm, preferably, 95 mm.

The lead titanate coating prepared herein can sequentially comprise a priming layer and a piezoelectric coating, or can sequentially comprise a piezoelectric coating and a wear-resistant layer, or can sequentially comprise a priming layer, a piezoelectric coating and a wear-resistant layer, and preferably, it sequentially comprises a priming layer, a piezoelectric coating and a wear-resistant layer.

The lead titanate coating prepared according to the present invention can be combined with the matrix closely, and the intensity of the piezoelectric signal is high. Therefore, the lead titanate coating can be widely applied to mechanical parts, such as a piston ring, a cylinder, a gear, and the like, to dynamically monitor the service situations of the parts better.

The present invention provides a gear, in which at least one surface of the tooth root and the tooth surface is coated with the lead titanate coating described above.

In the present invention, the tooth root and/or the tooth surface of the gear is a matrix for the coating. In the present invention, there is no specific limitation on the size, model, material and processing mode of the gear or the like. Instead, it can optionally be any commonly-used gear in the art. The problems of the gear provided by the present invention, such as crackles on its root, rupture and tooth lost during service and damage on the surface of the tooth thereof, can be better monitored in real time due to being coated with the lead titanate coating described above, which facilitates its applications.

With reference to FIG. 6, it is a schematic diagram showing the gear provided by an example of the present invention. In FIG. 6, the numeral 61 represents a tooth root, the numeral 62 represents a piezoelectric coating (lead titanate coating) covering the tooth root 61, and the numeral 63 represents a wear-resistant layer (Fe—Cr—B—Si layer) covering the piezoelectric coating 62.

The force bearing will necessarily change before a crackle is generated on the tooth root of the gear or before the tooth is broken, and variation in the force can be converted by the lead titanate coating thereon into variation in the electric charge. By monitoring the variation in the electric charge exported, the change in the position and shape of the tooth root of the gear can be indirectly monitored.

The processing method of a gear provided according to one embodiment of the present invention comprises: providing a gear; spraying a mixed powder to the tooth root of the gear, and subjecting it to polarization to produce a gear with a lead titanate coating, wherein the mixed powder comprises PbTiO$_3$ powder, PbO powder and Al powder.

Alternatively, the processing method of a gear provided according to one embodiment of the present invention comprises: providing a gear; spraying a mixed powder to the tooth root of the gear to form a coating, wherein the mixed powder comprises PbTiO$_3$ powder, PbO powder and Al powder; forming a wear-resistant layer on the coating by spraying; and then subjecting it to polarization, to produce a gear with the lead titanate coating.

Alternatively, the processing method of a gear provided according to one embodiment of the present invention comprises: providing a gear; forming a priming layer on the tooth root of the gear by spraying; spraying a mixed powder to the priming layer on the tooth root of the gear to form a coating, wherein the mixed powder comprises PbTiO$_3$ powder, PbO powder and Al powder; forming a wear-resistant layer on the coating by spraying, and then subjecting it to polarization, to produce a gear with the lead titanate coating.

With reference to FIG. 7, it is a schematic diagram showing a gear provided by another embodiment of the present invention. In FIG. 7, the numeral 71 represents a tooth surface, the numeral 72 represents a piezoelectric coating (lead titanate coating) covering the tooth surface 71, and the numeral 73 represents a wear-resistant layer (Fe—Cr—B—Si layer) covering the piezoelectric coating 72.

The gear includes the light loading gear. During service, the tooth surface will suffer from continuous abrasion. For the gear with the composite coating having wear resistant and self-monitoring properties provided by embodiments of the present invention, the force bearing will change with continuous abrasion of the tooth surface. The slight variation in the force will be converted to variation in the electric charge by the lead titanate coating. By monitoring the variation in the electric charge exported, the wearing process and change in the wearing position of the tooth surface of the gear can be indirectly monitored.

The processing method of a gear provided according to one embodiment of the present invention comprises: providing a gear; spraying a mixed powder to the tooth surface of the gear; and subjecting it to polarization, to produce a gear with a lead titanate coating, wherein the mixed powder comprises $PbTiO_3$ powder, PbO powder and Al powder.

Alternatively, the processing method of a gear provided according to one embodiment of the present invention comprises: providing a gear; spraying a mixed powder to the tooth surface and the tooth root of the gear; and subjecting it to polarization, to produce a gear with a lead titanate coating, wherein the mixed powder comprises $PbTiO_3$ powder, PbO powder and Al powder.

It should be noted that, the combination and the specific processes for the preparation methods of the lead titanate coating are described above, which will not be particularly limited herein.

The gear provided by the present invention has the lead titanate coating described above, which corresponds to be equipped with a better self-detecting system. Before severe damages of the gear, such as tooth breaking, occur, the damages situations can be monitored and an alarm will be given in time, so that measures can be decidedly taken when problems appear, and serious results resulted from failure of the surface coating will be avoided.

The present invention provides a cylinder and piston assembly, in which at least one contact surface of the supporting surfaces of the piston ring and the cylinder wall is sprayed with the lead titanate coating described above.

In the present invention, the internal surfaces of the cylinder wall and/or the supporting surface of the piston ring in the cylinder and piston assembly (cylinder and piston set) are the matrix for the coating. In the present invention, there is no particular limitation on the size, model, material and processing mode of the cylinder and piston set or the like, which can be prepared by traditional preparation processes.

The lead titanate coating can be arranged on one side or both sides of the internal surfaces of the cylinder wall, or can be arranged on one side or both sides of the supporting surfaces of the piston ring. That is, the lead titanate coating can be arranged on any combination of these sides.

The damage process on the surface of the piston and the cylinder in the cylinder and piston set provided herein can be better monitored in real time, due to being coated with the lead titanate coating described above, which facilitates applications.

With reference to FIG. 8, it is a schematic diagram showing the cylinder and piston assembly provided by an embodiment of the present invention. In FIG. 8, the numeral 81 represents a side of the internal surfaces of the cylinder wall, the numeral 82 represents a piezoelectric coating (lead titanate layer) covering one side 81 of the internal surfaces of the cylinder wall, and the numeral 83 represents a wear-resistant layer (Fe—Cr—B—Si layer) covering the piezoelectric coating 82. With reference to FIG. 9, it is a schematic diagram showing the cylinder and piston assembly provided by another embodiment of the present invention. In FIG. 9, the numeral 91 represents a side of the supporting surfaces of the piston ring, the numeral 92 represents a piezoelectric coating (lead titanate layer) covering one side 91 of the supporting surfaces of the piston ring, and the numeral 93 represents a wear-resistant layer (Fe—Cr—B—Si layer) covering the piezoelectric coating 92.

During the service of the piston and the cylinder wall, abrasion continuously occurs on the contact surface, i.e., the internal surfaces of the cylinder wall and the supporting surfaces of the piston ring. For the cylinder and piston set with the composite coating having wear resistant and self-monitoring properties provided by embodiments of the present invention, the force bearing will change with continuous abrasion of the contact surface. The variation in the force will be converted to variation in the electric charge by the lead titanate coating. By monitoring the variation in the electric charge exported, the wearing process and change in the wearing position of the cylinder and piston can be indirectly monitored.

The processing method for a cylinder and piston assembly provided by an embodiment of the present invention comprises: providing a piston and a cylinder; spraying a mixed powder to at least one contact surface of the cylinder wall and the supporting surface of the piston ring; and subjecting it to polarization, to produce a cylinder and piston assembly with the lead titanate coating; wherein the mixed powder comprises $PbTiO_3$ powder, PbO powder and Al powder.

In a similar way, the combination of preparation methods of the lead titanate coating and specific processes are as described above. Besides, the cylinder and the piston provided by embodiments of the present invention can be prepared by traditional preparation processes. After the cylinder wall has been prepared by a traditional preparation process, a wear-resistant composite coating is sprayed on the internal surface thereof. Since it is not convenient to spray the internal surface through a large nozzle, spin spraying through a small nozzle can be used, so that the inside of the cylinder wall can be sprayed with the wear-resistant composite coating above.

The cylinder and piston assembly provided herein is coated with the lead titanate coating described above, so that sliding abrasion on the surface can be better monitored, which facilitates applications.

The invention further provides a sensing system for matrix surface failure, which comprises: a sensing device; and a signal analysis device for analyzing the signal output of the sensing device. The sensing device comprises a sensing unit comprising: the lead titanate coating described above covering the surface of the matrix, which is used to perceive and convert the signal about the matrix surface failure; and the first electrode arranged on the lead titanate coating, which is used to output the signal about the matrix surface failure.

The sensing system provided herein adopts the lead titanate coating described above for enhancing the intensity of the piezoelectric signal, which can be used to better monitor a series of failure forms of the parts, such as abrasion and crackles, and to provide pre-warning.

With reference to FIG. 10, it is a schematic diagram showing the process of abrasion test of the sensing system provided by an example of the present invention. In FIG. 10, the numeral 1 represents a surface of the part, the numeral 211 represents a piezoelectric coating (sensing layer) covering the surface 1 of the part, the numeral 212 represents a wear-resistant layer covering the piezoelectric coating 211, the numeral 22 represents a first electrode arranged on the piezoelectric coating 211, the numeral 3 represents a electric charge amplifier, and the numeral 4 is a data analysis device.

In the sensing device of the present invention, the signal for matrix surface failure can be better sensed by the sensing unit composed of the lead titanate coating described above and the first electrode thereon.

The lead titanate coating covers the surface of the matrix. The force bearing thereof varies with continuous abrasion of the matrix surface. The slight variation in the force can be converted to variation in the electric charge by the lead titanate coating. The matrix is the second electrode, and a current export electrode is constituted by the first electrode and the second electrode to output the electrical signal.

The matrix is preferably a metallic matrix, and more preferably is 45# steel. That is, the matrix can be a moving parts of a steam turbine, a compressor, and a pump, and also can be parts, such as gear, shaft and piston pin etc. (the parts should be subjected to high-frequency quenching, or flame surface quenching), and further can be a cast. Alternatively, the matrix can be a copper matrix or an aluminum matrix, so as to be suitable for parts used in other applications.

The lead titanate coating is as described above, and will not be further illustrated below.

The first electrode 22 is preferably a gold electrode, so as to enhance the conductivity and reduce the current loss. The first electrode is formed on the surface of the lead titanate coating by a coating process. In order to obtain a gold electrode with a more uniform thickness, the gold electrode is preferably formed by coating for 3 times. In addition, since the matrix is a metallic matrix, and the priming layer is a nickel-aluminum alloy layer, the matrix or the priming layer can be used as the second electrode for exporting the current generated by the coating.

It should be noted that, silver electrode or aluminum electrode can also be selected as the first electrode as desired, and there is no limitation on specific materials. In an embodiment, gold electrode is selected in order to achieve better conductivity. Moreover, the first electrode is arranged at the non-abrasion part of the coating, to avoid the influence on the first electrode due to abrasion of the matrix coating.

Preferably, the sensing device described herein further comprises a signal amplification unit for amplifying the electrical signal output from the sensing unit, which facilitates displaying, recording and processing. The signal amplification unit, such as charge amplifier 3 or the like, will collect and amplify the weak signals perceived for further analysis. The signal amplitude can be enhanced from 15 to 200 by the charge amplifier 3, so that the signal wave can be more clearly and intuitively analyzed.

Preferably, the sensing device described herein further comprises a signal transformation unit, which can convert the electrical signal outputted from the sensing unit or the signal amplification unit to an electrical signal useful for displaying, recording and processing. An oscilloscope is a kind of signal transformation unit capable of exporting a signal in a mode of waveform.

In addition to the sensing device above, the sensing system described herein further comprises a signal analysis device for analyzing the signal outputted from the sensing device.

The signal analysis device is also referred as data analysis device, which is generally an electronic computer (computer analysis device), in which software for wavelet analysis and infra-red analysis can be installed. The analysis process can be performed on the signal taken or collected by various means, to achieve dynamical monitoring of the damages on the abrasion surface.

In the process of abrasion test in the embodiments above, a load is placed on the wear-resistant layer 212. The force bearing varies with continuous abrasion of the surface 1 of the part. The piezoelectric coating 211 will convert slight variation in the force into variation in the electric charge. The surface 1 of the part is the second electrode, and a current export electrode is constituted by the first electrode 22 and the second electrode 1 to output the electrical signal. The electrical signal is amplified and exported by a charge amplifier 3. Finally, the signal is analyzed by a data analysis device 4.

The sensing system described herein is with respect to the surface failure of a matrix, which can perceive and monitor a crackle with wideness from 1 μm to 1 mm, and also can monitor propagation of a fine crackle having a length of about 1 μm and a width of about 1 μm.

Figure 11:
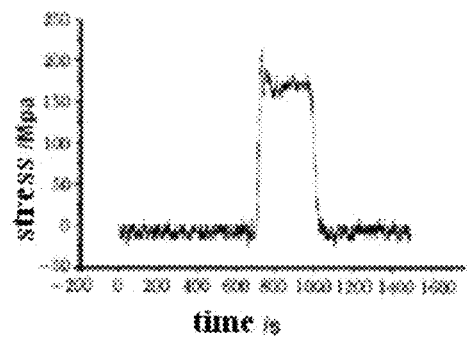
FIG. 11 is a waveform signal recorded by the sensing system described in the present invention.
Figure 12:
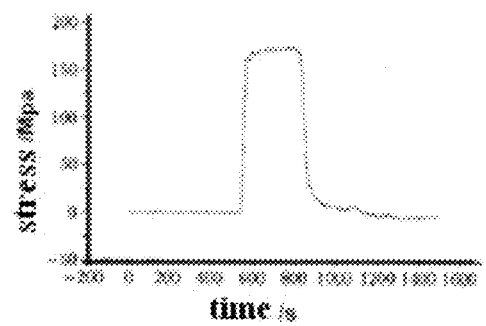
FIG. 12 is a waveform signal recorded by resistance strain gauge.

For the surface failure situations of the same matrix, the detection results for the sensing system described herein and the electrical resistance strain gauge were shown in FIG. 11 and FIG. 12. FIG. 11 is the waveform signal recorded by the sensing system described herein, and FIG. 12 is the waveform signal recorded by the electrical resistance strain gauge. As can be seen from FIGS. 11 and 12, the sensing system described herein has excellent sensing sensitivity, is capable of on-line monitor the service situation of the parts in real time, and determine the failure form of the parts, so that it is helpful for improving the process and enhancing the industrial productivity.

For better understanding of the present invention, the lead titanate coating provided herein and the preparing method thereof will be described in detail with reference to examples below.

In the following examples, supersonic plasma spraying is performed by high-performance GTV F6 plasma spraying equipment; $PbTiO_3$ powder is purchased under the trademark of P-5H from Baoding Hongsheng Acoustics Electron Apparatus Co., Ltd.; and the remaining powders are from Beijing General Research Institute of Mining & Metallurgy, with purities of 99.99%.

Example 1

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 20 meshes as the sand, and the abrasive blasting process comprised: an abrasive blasting pressure of 0.6 MPa, an abrasive blasting angle of 45°, and an abrasive blasting distance of 145 mm.

After abrasive blasting, the matrix was heat-treated to reach a temperature of 120° C.

A priming layer having a thickness of 20 μm was formed on the matrix by supersonic plasma spraying using NiAl alloy powders with particle size of 30 μm, and the spraying process comprised: a spraying voltage of 120 V, a spraying current of 385 A, a spraying power of 40 kW, and a spraying distance of 110 mm.

A mixed powder was sprayed on the priming layer of the matrix through supersonic plasma to form a coating having a thickness of 50 μm, wherein the mixed powder comprised powder of spherical $PbTiO_3$ particles with particle size of 40 μm, PbO powder with a particle size of 70 μm and Al powder with a particle size of 30 μm in a ratio by mass of 7:1:2. The spraying process comprised: a spraying voltage of 120 V, a spraying current of 450 A, a spraying power of 55 kW, and a spraying distance of 110 mm.

A wear-resistant layer having a thickness of 100 μm was formed on the coating by supersonic plasma spraying using Fe—Cr—B—Si powder with particle size of 50 μm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.4 KV/mm.

Figure 13:
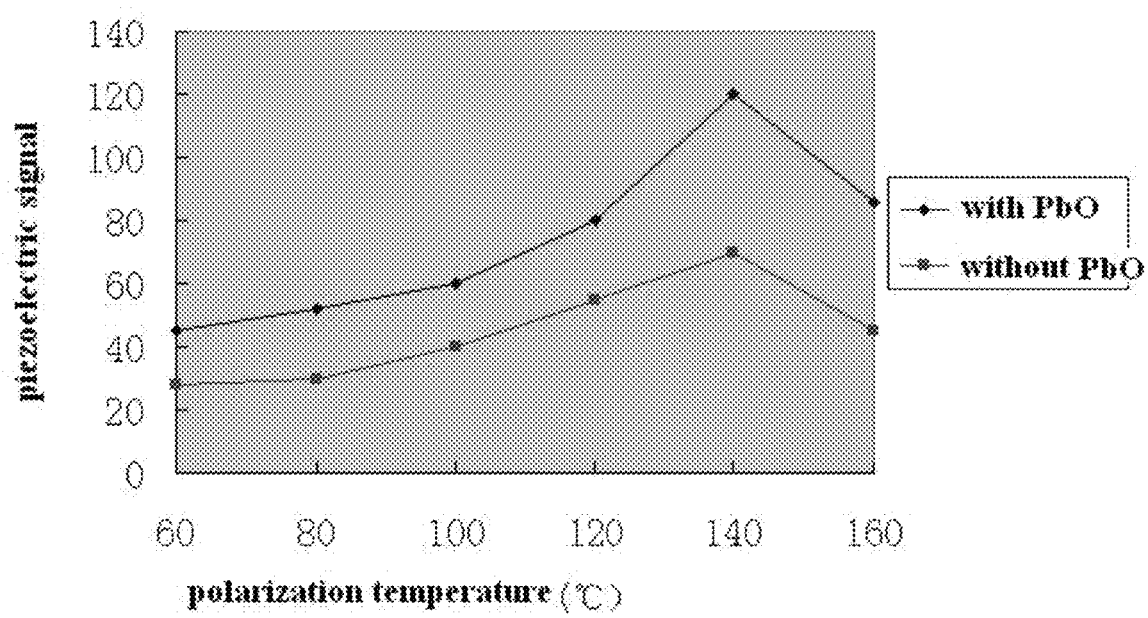
FIG. 13 is a graph showing the piezoelectric signal of the coatings provided by Examples 1-6 of the present invention and Comparative Examples 1-6 as a function of the polarization temperature.

According to the method described above, the piezoelectric signal of the lead titanate coating was measured. The results are shown in FIG. 13, which is a graph showing the piezoelectric signal of the coatings provided by Examples 1-6 of the present invention and Comparative Examples 1-6 as the function of the polarization temperature. As can be seen from FIG. 13, the coating prepared according to Example 1 of the present invention has a relatively strong piezoelectric signal.

According to the method described above, the cross section of the lead titanate coating was observed. The results are shown in FIG. 14, which shows the cross-sectional morphology of the coating provided by Example 1 of the present invention. As can be seen from FIG. 14, the coating prepared according to Example 1 of the present invention is well combined with the matrix.

Examples 2-6

The matrices with a lead titanate coating were obtained according to the method of Example 1, except that the polarization temperature was changed to 60° C., 80° C., 100° C., 140° C. and 160° C., respectively.

According to the method described above, the piezoelectric signal of the lead titanate coating was measured. The results are shown in FIG. 13. As can be seen from FIG. 13, the coatings prepared according to Example 1-6 of the present invention have relatively strong piezoelectric signals, and maximal piezoelectric signal is obtained at temperature approaching 120° C.

Comparative Examples 1-6

The matrices with the lead titanate coating were obtained according to the method of Example 1, except that PbO powder was excluded from the mixed powder, the ratio of $PbTiO_3$ powder to Al powder was 7:3, and the polarization temperature was 120° C., 60° C., 80° C., 100° C., 140° C. and 160° C., respectively.

According to the method described above, the piezoelectric signal of the lead titanate coatings was measured. The results are shown in FIG. 13. As can be seen from FIG. 13, the piezoelectric signal of the coatings without PbO powder was poorer than that of the coatings comprising PbO powder provided by Examples of the present invention.

According to the method described above, the cross section of the lead titanate coating was observed. The results are shown in FIG. 15, which shows the cross-sectional morphology of the coating provided by Comparative Example 1 of the present invention. As can be seen from FIG. 15, the coating without PbO powder is poorly combined with the matrix.

Example 7

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 16 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A priming layer having a thickness of 20 μm was formed on the matrix by supersonic plasma spraying using NiAl alloy powders with particle size of 50 μm, and the spraying process comprised: a spraying voltage of 120 V, a spraying current of 380 A, a spraying power of 45 kW, and a spraying distance of 105 mm.

A mixed powder was sprayed on the priming layer of the matrix through supersonic plasma to form a coating having a thickness of 50 μm, wherein the mixed powder comprised powder of spherical $PbTiO_3$ particles with particle size of 60 μm, PbO powder with a particle size of 40 μm and Al powder with a particle size of 40 μm in a ratio by mass of 7:1:2. The spraying process comprised: a spraying voltage of 120 V, a spraying current of 440 A, a spraying power of 60 kW, and a spraying distance of 100 mm.

A wear-resistant layer having a thickness of 100 μm was formed on the coating by supersonic plasma spraying using Fe—Cr—B—Si powder with particle size of 60 μm. The spraying process comprised: a spraying voltage of 120 V, a spraying current of 420 A, a spraying power of 45 kW, and a spraying distance of 100 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.6 KV/mm.

According to the method described above, the piezoelectric signal of the lead titanate coating was measured. The results are shown in FIG. 16, which is a graph showing the piezoelectric signal of the coatings provided by Examples 7-11 of the present invention and Comparative Examples 7-11 as the function of the polarization temperature. As can be seen from FIG. 16, the coating prepared according to Example 7 of the present invention has stronger piezoelectric signal.

Figure 17:
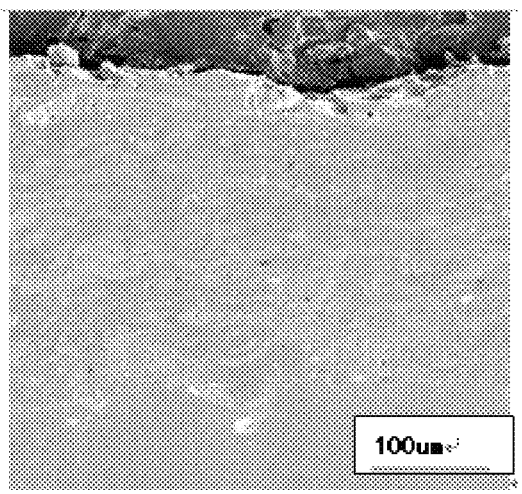
FIG. 17 shows the cross-sectional morphology of the coating provided by Example 7 of the present invention.

According to the method described above, the section of the lead titanate coating was observed. The results are shown in FIG. 17. FIG. 17 showed the cross-sectional morphology of the coating provided by Example 7 of the present invention. As can be seen from FIG. 17, the coating prepared according to Example 7 of the present invention is well combined with the matrix, and the particles were melted homogeneously.

Examples 8-11

The matrices with the lead titanate coating were obtained according to the method of Example 7, except that the polarization temperature was changed to 60° C., 80° C., 100° C., and 140° C., respectively.

According to the method described above, the piezoelectric signal of the lead titanate coating was measured. The results are shown in FIG. 16. As can be seen from FIG. 16, the coatings prepared according to Examples 7-11 of the present invention have relatively strong piezoelectric signals, and maximal piezoelectric signal was obtained at temperature approaching 120° C.

Comparative Examples 7-11

The matrices with the lead titanate coating were obtained according to the method of Example 7, except that Al powder was excluded from the mixed powder, the ratio of $PbTiO_3$ powder to PbO powder was 7:3, and the polarization temperature was 120° C., 60° C., 80° C., 100° C., and 140° C., respectively.

According to the method described above, the piezoelectric signal of the lead titanate coating was measured. The results are shown in FIG. 16. As can be seen from FIG. 16, the piezoelectric signal of the coating without Al powder was poorer than that of the coating comprising Al powder provided according to Examples of the present invention.

Figure 18:
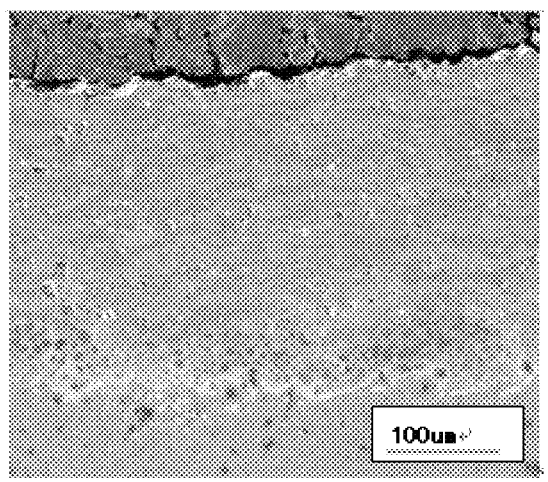
FIG. 18 shows the cross-sectional morphology of the coating provided by Comparative Example 7 of the present invention.

According to the method described above, the cross section of the lead titanate coating was observed. The results are shown in FIG. 18, which shows the cross-sectional morphology of the coating provided by Comparative Example 7 of the present invention. As can be seen from FIG. 18, the coating without Al powder is poorly combined with the matrix.

Based on the Examples and Comparative Examples above, it can be seen that both the functions of the PbO powder and the Al powder can not be underestimated in the coating according to the present invention.

Example 12

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 20 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A priming layer having a thickness of 20 μm was formed on the matrix by supersonic plasma spraying using NiAl alloy powders with particle size of 40 μm, and the spraying process comprised: a spraying voltage of 120 V, a spraying current of 380 A, a spraying power of 45 kW, and a spraying distance of 105 mm.

A mixed powder was sprayed on the priming layer of the matrix through supersonic plasma to form a coating having a thickness of 50 μm, wherein the mixed powder comprised powder of spherical $PbTiO_3$ particles with particle size from 40 μm to 60 μm, PbO powder with a particle size of 50 μm and Al powder with a particle size of 35 μm in a ratio by mass of 7:1:2. The spraying process comprised: a spraying voltage of 120 V, a spraying current of 440 A, a spraying power of 60 kW, and a spraying distance of 100 mm.

A wear-resistant layer having a thickness of 100 μm was formed on the coating by supersonic plasma spraying using Fe—Cr—B—Si powder with particle size of 55 μm. The spraying process comprised: a spraying voltage of 120 V, a spraying current of 420 A, a spraying power of 45 kW, and a spraying distance of 100 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 19:
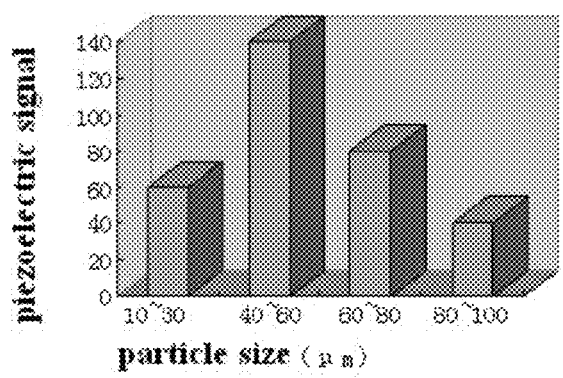
FIG. 19 is a graph showing the piezoelectric signal of the coatings provided by Example 12-15 of the present invention.

According to the method described above, the piezoelectric signal of the lead titanate coating was measured. The results are shown in FIG. 19, which is a graph showing the piezoelectric signal of the coatings provided by Examples 12-15 of the present invention. As can be seen from FIG. 19, the coating prepared according to Example 12 of the present invention has a relatively strong piezoelectric signal.

Examples 13-15

The matrices with the lead titanate coating were obtained according to the method in Example 12, except that the particle size of the $PbTiO_3$ powder was changed to be in the range from 10 μm to 30 μm, from 60 μm to 80 μm, and from 80 μm to 100 μm, respectively.

According to the method described above, the piezoelectric signal of the lead titanate coating was measured. The results are shown in FIG. 19. As can be seen from FIG. 19, the coatings prepared according to Examples 12-15 of the present invention have relatively strong piezoelectric signals, in which the coating possessing the $PbTiO_3$ powder with the particle size in the range from 40 μm to 60 μm is the best.

Example 16

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 16 meshes as the sand, and the abrasive blasting process comprised: an abrasive blasting pressure of 0.6 MPa, an abrasive blasting angle of 45°, and an abrasive blasting distance of 145 mm.

After abrasive blasting, the matrix was heat-treated to reach a temperature of 120° C.

A priming layer having a thickness of 20 μm was formed on the matrix by supersonic plasma spraying using NiAl alloy powders with particle size of 35 μm, and the spraying process comprised: a spraying voltage of 120 V, a spraying current of 385 A, a spraying power of 40 kW, and a spraying distance of 110 mm.

A mixed powder was sprayed on the priming layer of the matrix through supersonic plasma to form a coating having a thickness of 30 μm, wherein the mixed powder comprised powder of spherical $PbTiO_3$ particles with particle size of 50 μm, PbO powder with a particle size of 60 μm and Al powder with a particle size of 35 μm in a ratio by mass of 7:1:2. The spraying process comprised: a spraying voltage of 120 V, a spraying current of 450 A, a spraying power of 55 kW, and a spraying distance of 110 mm.

A wear-resistant layer having a thickness of 100 μm was formed on the coating by supersonic plasma spraying using Fe—Cr—B—Si powder with particle size of 55 μm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 20:
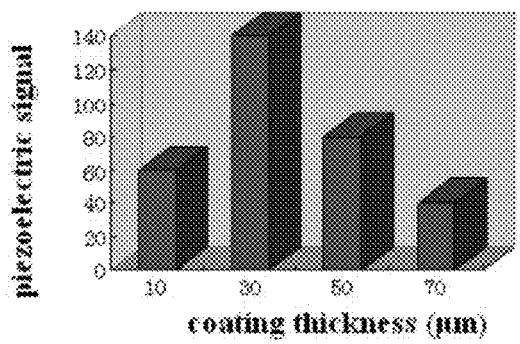
FIG. 20 is a graph showing the piezoelectric signal of the coatings provided by Examples 16-19 of the present invention.

According to the method described above, the piezoelectric signal of the lead titanate coating was measured. The results are shown in FIG. 20, which is a graph showing the piezoelectric signal of the coatings provided by Examples 16-19 of the present invention. As can be seen from FIG. 20, the coating prepared according to Example 16 of the present invention had a stronger piezoelectric signal.

Figure 21:
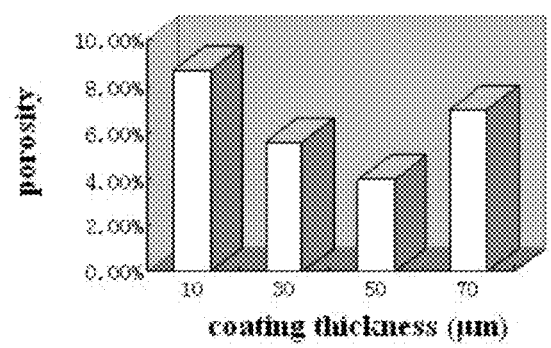
FIG. 21 is a graph showing the porosity of the coatings provided by Examples 16-19 of the present invention.

According to the method described above, the porosity of the lead titanate coating was measured. The results are shown in FIG. 21, which is a graph showing the porosity of the coatings provided by Examples 16-19 of the present invention. As can be seen from FIG. 21, the porosity of the coating prepared according to Example 16 of the present invention is lower.

Examples 17-19

Except that coatings having thickness of 10 μm, 50 μm, and 70 μm, respectively, were formed by spraying the mixed powder to the priming layers of the matrices, the matrices with the lead titanate coating were finally prepared according to the method in Example 16.

According to the method described above, the piezoelectric signal of the lead titanate coating was measured. The results are shown in FIG. 20. As can be seen from FIG. 20, the coatings prepared according to Examples 16-19 of the present invention have stronger piezoelectric signals, in which the best result is achieved when the coating formed by the piezoelectric material has a thickness of 30 μm.

According to the method described above, the porosity of the lead titanate coating was measured. The results are shown in FIG. 21. As can be seen from FIG. 21, the coatings prepared according to Examples 16-19 of the present invention have smaller porosity, in which the best result is achieved when the coating formed by the piezoelectric material has a thickness of 50 μm.

Example 20

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 24 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A priming layer having a thickness of 20 μm was formed on the matrix by supersonic plasma spraying using NiAl alloy powders with particle size of 35 μm, and the spraying process comprised: a spraying voltage of 120 V, a spraying current of 385 A, a spraying power of 40 kW, and a spraying distance of 110 mm.

A mixed powder was sprayed on the priming layer of the matrix through supersonic plasma to form a coating having a thickness of 50 μm, wherein the mixed powder comprised powder of spherical $PbTiO_3$ particles with particle size of 55 μm, PbO powder with a particle size of 60 μm and Al powder with a particle size of 35 μm in a ratio by mass of 7:1:2. The spraying process comprised: a spraying voltage of 120 V, a spraying current of 430 A, a spraying power of 55 kW, and a spraying distance of 90 mm.

A wear-resistant layer having a thickness of 100 μm was formed on the coating by supersonic plasma spraying using Fe—Cr—B—Si powder with particle size of 55 μm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 22:
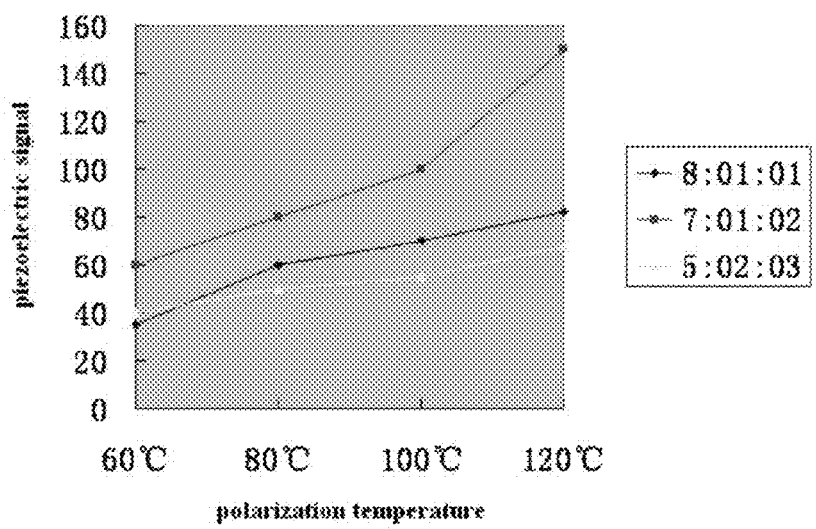
FIG. 22 is a graph showing the piezoelectric signal of the coatings provided by Examples 20-31 of the present invention.

According to the method described above, the piezoelectric signal of the lead titanate coating was measured. The results are shown in FIG. 22, which is a graph showing the piezoelectric signal of the coatings provided by Examples 20-31 of the present invention. As can be seen from FIG. 22, the coating prepared according to Example 20 of the present invention has a stronger piezoelectric signal.

Examples 21-23

The matrices with the lead titanate coating were obtained according to the method in Example 20, except that the polarization temperature was changed to be 60° C., 80° C., and 100° C., respectively.

According to the method described above, the piezoelectric signal of the lead titanate coating was measured. The results are shown in FIG. 22. As can be seen from FIG. 22, the coatings prepared according to Examples 20-23 of the present invention have stronger piezoelectric signals, in which the best result is achieved at the polarization temperature approaching 120° C.

Examples 24-27

The matrices with the lead titanate coating were obtained according to the method in Example 20, except that the mass ratio of these 3 components in the mixed powder was 8:1:1, and the polarization temperature was 60° C., 80° C., 100° C., and 120° C., respectively.

According to the method described above, the piezoelectric signal of the lead titanate coating was measured. The results are shown in FIG. 22. As can be seen from FIG. 22, the coatings prepared according to Examples 24-27 of the present invention have stronger piezoelectric signals, in which the best result is achieved at the polarization temperature approaching 120° C.

Examples 28-31

The matrices with the lead titanate coating were obtained according to the method in Example 20, except that the mass ratio of these 3 components in the mixed powder was 5:2:3, and the polarization temperature was 60° C., 80° C., 100° C., and 120° C., respectively.

According to the method described above, the piezoelectric signal of the lead titanate coating was measured. The results are shown in FIG. 22. As can be seen from FIG. 22, the coatings prepared according to Examples 28-31 of the present invention have stronger piezoelectric signals, in which the best result is achieved at the polarization temperature approaching 120° C.

As can be seen from the Examples above, the coating exhibits the best performance when the mass ratio of the $PbTiO_3$ powder, the PbO powder and the Al powder in the mixed powder was 7:1:2.

Example 32

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 24 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A priming layer having a thickness of 30 μm was formed on the matrix by supersonic plasma spraying using NiAl alloy powders with particle size of 30 μm, and the spraying process comprised: a spraying voltage of 120 V, a spraying current of 385 A, a spraying power of 45 kW, and a spraying distance of 110 mm.

A mixed powder was sprayed on the priming layer of the matrix through supersonic plasma to form a coating having a thickness of 50 μm, wherein the mixed powder comprised powder of spherical $PbTiO_3$ particles with particle size of 50 μm, PbO powder with a particle size of 65 μm and Al powder with a particle size of 40 μm in a ratio by mass of 7:1:2. The spraying process comprised: a spraying voltage of 120 V, a spraying current of 450 A, a spraying power of 55 kW, and a spraying distance of 90 mm.

A wear-resistant layer having a thickness of 100 μm was formed on the coating by supersonic plasma spraying using Fe—Cr—B—Si powder with particle size of 50 μm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 23:
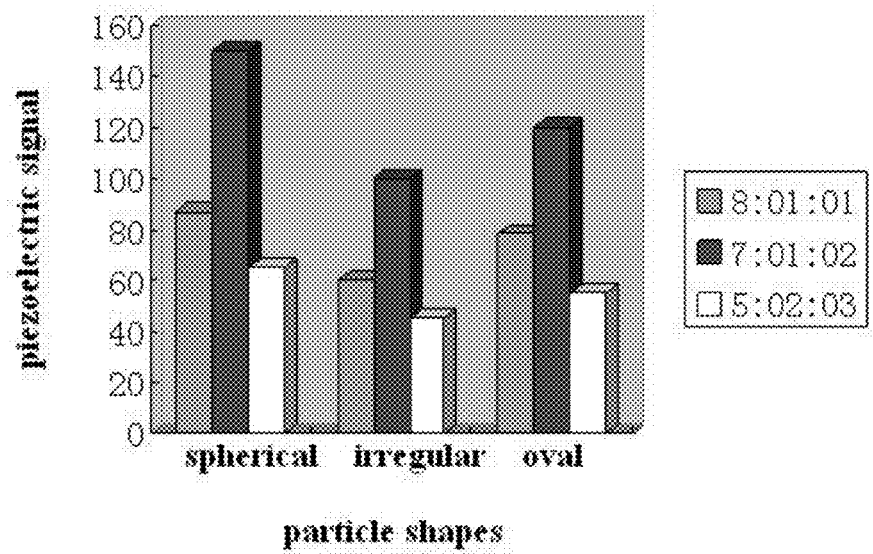
FIG. 23 is a graph showing the piezoelectric signal of the coatings provided by Examples 32-40 of the present invention.

According to the method described above, the piezoelectric signal of the lead titanate coating was measured. The results are shown in FIG. 23, which is a graph showing the piezoelectric signals of the coatings provided by Examples 32-40 of the present invention. As can be seen from FIG. 23, the coating prepared according to Example 32 of the present invention has a stronger piezoelectric signal.

Figure 24:
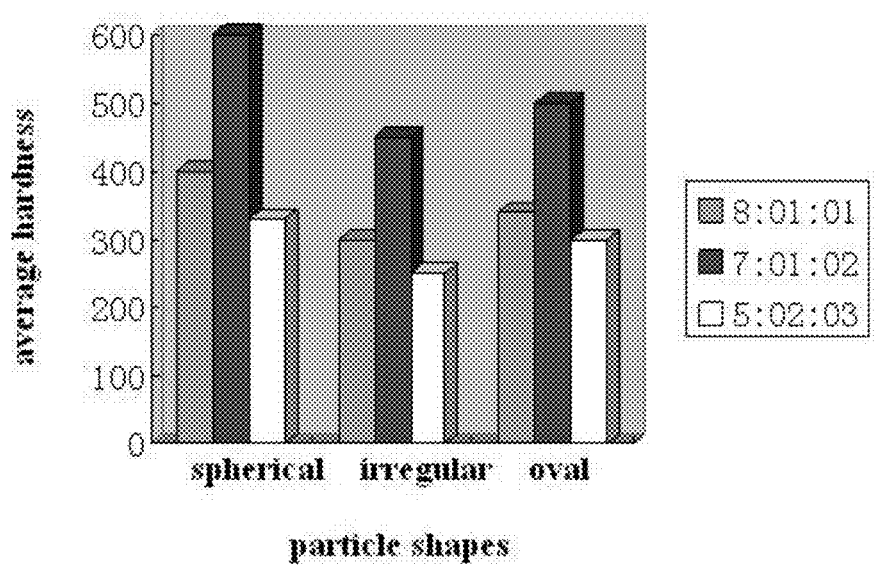
FIG. 24 is a graph showing the average hardness of the coatings provided by Examples 32-40 of the present invention.

According to the method described above, the average hardness of the lead titanate coating was tested. The results are shown in FIG. 24, which is a graph showing the average hardness of the coatings provided by Examples 32-40 of the present invention. As can be seen from FIG. 24, the coating prepared according to Example 32 of the present invention has a higher hardness.

Examples 33 and 34

The matrices with the lead titanate coating were prepared according to the method in Example 32, except that powder of irregular $PbTiO_3$ particles and powder of oval $PbTiO_3$ particles were employed.

According to the method described above, the piezoelectric signal of the lead titanate coating was measured. The results are shown in FIG. 23. As can be seen from FIG. 23, the coating prepared according to Examples 32-34 of the present invention have stronger piezoelectric signal, in which the best result is achieved when powder of spherical $PbTiO_3$ particles is used.

According to the method described above, the average hardness of the lead titanate coating was tested. The results are shown in FIG. 24. As can be seen from FIG. 24, the coating prepared according to Examples 32-34 of the present invention have higher hardness, in which the best result is achieved when powder of spherical $PbTiO_3$ particles is used.

Example 35

The matrices with the lead titanate coating were prepared according to the method in Example 32, except that the mass ratio of these 3 components in the mixed powder was 8:1:1.

According to the method described above, the piezoelectric signal of the lead titanate coating was measured. The results are shown in FIG. 23. As can be seen from FIG. 23, the coating prepared according to Example 35 of the present invention has a stronger piezoelectric signal.

According to the method described above, the average hardness of the lead titanate coating was tested. The results are shown in FIG. 24. As can be seen from FIG. 24, the coating prepared according to Example 35 of the present invention has higher hardness.

Examples 36 and 37

The matrices with the lead titanate coating were prepared according to the method in Example 35, except that powder of irregular $PbTiO_3$ particles and powder of oval $PbTiO_3$ particles were employed.

According to the method described above, the piezoelectric signal of the lead titanate coating was measured. The results are shown in FIG. 23. As can be seen from FIG. 23, the coatings prepared according to Examples 35-37 of the present invention have stronger piezoelectric signals, in which the best result is achieved when powder of spherical $PbTiO_3$ particles is used.

According to the method described above, the average hardness of the lead titanate coating was tested. The results are shown in FIG. 24. As can be seen from FIG. 24, the coatings prepared according to Examples 35-37 of the present invention have higher hardness, in which the best result is achieved when powder of spherical $PbTiO_3$ particles is used.

Example 38

The matrices with the lead titanate coating were prepared according to the method in Example 32, except that the mass ratio of these 3 components in the mixed powder was 5:2:3.

According to the method described above, the piezoelectric signal of the lead titanate coating was measured. The results are shown in FIG. 23. As can be seen from FIG. 23, the coating prepared according to Example 38 of the present invention has a stronger piezoelectric signal.

According to the method described above, the average hardness of the lead titanate coating was tested. The results are shown in FIG. 24. As can be seen from FIG. 24, the coating prepared according to Example 38 of the present invention has higher hardness.

Examples 39 and 40

The matrices with the lead titanate coating were prepared according to the method in Example 38, except that powder of irregular $PbTiO_3$ particles and powder of oval $PbTiO_3$ particles were employed.

According to the method described above, the piezoelectric signal of the lead titanate coating was measured. The results are shown in FIG. 23. As can be seen from FIG. 23, the coatings prepared according to Examples 38-40 of the present invention have stronger piezoelectric signals, in which the best result is achieved when powder of spherical $PbTiO_3$ particles is used.

According to the method described above, the average hardness of the lead titanate coating was tested. The results are shown in FIG. 24. As can be seen from FIG. 24, the coatings prepared according to Examples 38-40 of the present invention have higher hardness, in which the best result is achieved when powder of spherical $PbTiO_3$ particles is used.

As can be seen from the Examples above, the coating exhibits best performance when the mass ratio of the $PbTiO_3$ powder, the PbO powder and the Al powder in the mixed powder is 7:1:2 and powder of spherical $PbTiO_3$ particles is used.

Example 41

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 24 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A priming layer having a thickness of 20 µm was formed on the matrix by supersonic plasma spraying using NiAl alloy powders with particle size of 35 µm, and the spraying process comprised: a spraying voltage of 120 V, a spraying current of 385 A, a spraying power of 40 kW, and a spraying distance of 110 mm.

A mixed powder was sprayed on the priming layer of the matrix through supersonic plasma to form a coating having a thickness of 50 µm, wherein the mixed powder comprised powder of spherical $PbTiO_3$ particles with particle size of 50 µm, PbO powder with a particle size of 70 µm and Al powder with a particle size of 40 µm in a ratio by mass of 7:1:2. The spraying process comprised: a spraying voltage of 120 V, a spraying current of 430 A, a spraying power of 55 kW, and a spraying distance of 100 mm.

A wear-resistant layer having a thickness of 100 µm was formed on the coating by supersonic plasma spraying using Fe—Cr—B—Si powder with particle size of 55 µm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 25:
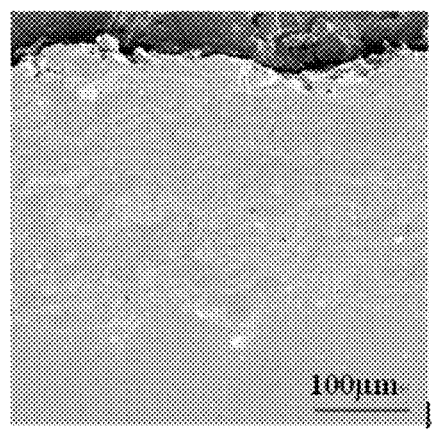
FIG. 25 shows the cross-sectional morphology of the coating provided by Example 41 of the present invention.

According to the method described above, the cross section of the lead titanate coating was observed. The results are shown in FIG. 25, which shows the cross-sectional morphology of the coating provided in Example 41 of the present invention. As can be seen from FIG. 25, the coating having a priming layer is well combined with the matrix.

Figure 26:
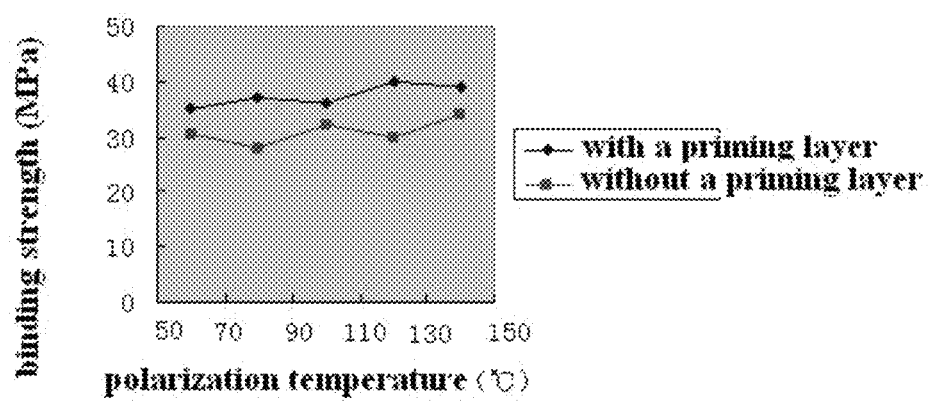
FIG. 26 is a graph showing the binding strength of the coating provided by Examples 41-50 of the present invention.

According to the method described above, the binding strength of the lead titanate coating was tested. The results are shown in FIG. 26, which is a graph showing the binding strength of the coatings provided by Examples 41-50 of the present invention. As can be seen from FIG. 26, the coating with a priming layer has higher binding strength.

Examples 42-45

The matrices with the lead titanate coating were obtained according to the method in Example 41, except that the polarization temperature was changed to be 60° C., 80° C., 100° C., and 140° C., respectively.

According to the method described above, the binding strength of the lead titanate coating was tested. The results are shown in FIG. 26. As can be seen from FIG. 26, the coating with a priming layer has higher binding strength, and the best result is achieved at the polarization temperature of 120° C.

Example 46

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 24 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A mixed powder was sprayed on the matrix through supersonic plasma to form a coating having a thickness of 50 µm, wherein the mixed powder comprised powder of spherical $PbTiO_3$ particles with particle size of 50 µm, PbO powder with a particle size of 70 µm and Al powder with a particle size of 40 µm in a ratio by mass of 7:1:2. The spraying process comprised: a spraying voltage of 120 V, a spraying current of 430 A, a spraying power of 55 kW, and a spraying distance of 100 mm.

A wear-resistant layer having a thickness of 100 µm was formed on the coating by supersonic plasma spraying using Fe—Cr—B—Si powder with particle size of 55 µm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 27:
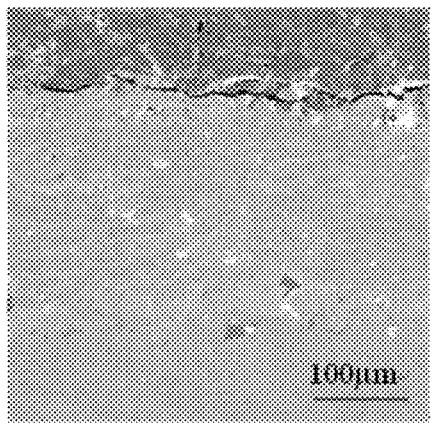
FIG. 27 shows the cross-sectional morphology of the coating provided by Example 46 of the present invention.

According to the method described above, the cross section of the lead titanate coating was observed. The results are shown in FIG. 27, which shows the cross-sectional morphology of the coating provided in Example 46 of the present invention. As can be seen from FIG. 27, the coating without a priming layer is poorly combined with the matrix.

According to the method described above, the binding strength of the lead titanate coating was tested. The results are shown in FIG. 26. As can be seen from FIG. 26, the coating without the priming layer has poorer binding strength.

Examples 47-50

The matrices with the lead titanate coating were obtained according to the method in Example 46, except that the polarization temperature was changed to be 60° C., 80° C., 100° C., and 140° C., respectively.

According to the method described above, the binding strength of the lead titanate coating was tested. The results are shown in FIG. 26. As can be seen from FIG. 26, the coating without the priming layer had poorer binding strength.

Example 51

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 24 meshes as the sand, and the abrasive blasting process comprised: an abrasive blasting pressure of 0.65 MPa, an abrasive blasting angle of 45°, and an abrasive blasting distance of 145 mm.

After abrasive blasting, the matrix was heat-treated to reach a temperature of 120° C.

A priming layer having a thickness of 20 μm was formed on the matrix by supersonic plasma spraying using NiAl alloy powders with particle size of 40 μm, and the spraying process comprised: a spraying voltage of 120 V, a spraying current of 390 A, a spraying power of 40 kW, and a spraying distance of 100 mm.

A mixed powder was sprayed on the priming layer of the matrix through supersonic plasma to form a coating having a thickness of 50 μm, wherein the mixed powder comprised powder of spherical $PbTiO_3$ particles with particle size of 50 μm, PbO powder with a particle size of 40 μm and Al powder with a particle size of 40 μm in a ratio by mass of 7:1:2. The spraying process comprised: a spraying voltage of 120 V, a spraying current of 430 A, a spraying power of 55 kW, and a spraying distance of 100 mm.

A wear-resistant layer having a thickness of 100 μm was formed on the coating by supersonic plasma spraying using Fe—Cr—B—Si powder with particle size of 55 μm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 28:
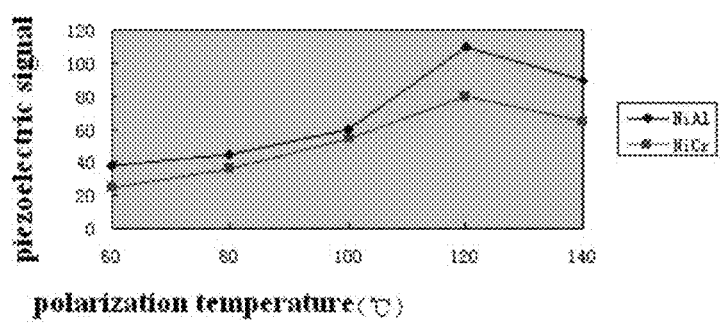
FIG. 28 is a graph showing the piezoelectric signal of the coating provided by Examples 51-60 of the present invention as a function of the polarization temperature.

According to the method described above, the piezoelectric signal of the lead titanate coating was measured. The results are shown in FIG. 28, which is a graph showing the piezoelectric signals of the coatings provided in Examples 51-60 of the present invention as a function of polarization temperature variation. As can be seen from FIG. 28, the coating prepared according to Example 51 of the present invention has a stronger piezoelectric signal.

Examples 52-55

The matrices with the lead titanate coating were obtained according to the method in Example 51, except that the polarization temperature was changed to be 60° C., 80° C., 100° C., and 140° C., respectively.

According to the method described above, the piezoelectric signal of the lead titanate coating was measured. The results are shown in FIG. 28. As can be seen from FIG. 28, the coatings prepared according to Examples 51-55 of the present invention have stronger piezoelectric signals, in which the best result is achieved at the polarization temperature of 120° C.

Example 56

The matrix with the lead titanate coating was obtained according to the method in Example 51, except that the powder for the priming layer was changed to be NiCr alloy.

According to the method described above, the piezoelectric signal of the lead titanate coating was measured. The result is shown in FIG. 28. As can be seen from FIG. 28, good result is observed when NiAl alloy is used as powder for the priming layer.

Examples 57-60

The matrices with the lead titanate coating were obtained according to the method in Example 56, except that the polarization temperature was changed to be 60° C., 80° C., 100° C., and 140° C., respectively.

According to the method described above, the piezoelectric signal of the lead titanate coating was measured. The result is shown in FIG. 28. As can be seen from FIG. 28, good result is observed when NiAl alloy is used as powder for the priming layer.

Example 61

45# steel matrix was provided after the oil stain on the surface thereof was cleaned using industrial caustic soda.

The matrix was subjected to quenching treatment, such that hardness of about HRC55 was achieved.

Abrasive blasting treatment was performed on the quenched matrix using brown corundum with a particle size of 24 meshes as the sand, and the abrasive blasting process comprised: an abrasive blasting pressure of 0.65 MPa, an abrasive blasting angle of 45°, and an abrasive blasting distance of 140 mm.

After abrasive blasting, the matrix was heat-treated to reach a temperature of 120° C.

A priming layer having a thickness of 20 μm was formed on the matrix by supersonic plasma spraying using NiAl alloy powders with particle size of 40 μm, and the spraying process comprised: a spraying voltage of 120 V, a spraying current of 390 A, a spraying power of 40 kW, and a spraying distance of 100 mm.

A mixed powder was sprayed on the priming layer of the matrix through supersonic plasma to form a coating having a thickness of 50 μm, wherein the mixed powder comprised powder of spherical $PbTiO_3$ particles with particle size of 50 μm, PbO powder with a particle size of 40 μm and Al powder with a particle size of 30 μm in a ratio by mass of 7:1:2. The spraying process comprised: a spraying voltage of 120 V, a spraying current of 440 A, a spraying power of 55 kW, and a spraying distance of 100 mm.

A wear-resistant layer having a thickness of 100 μm was formed on the coating by supersonic plasma spraying using Fe—Cr—B—Si powder with particle size of 55 μm. The spraying process comprised: a spraying voltage of 120 V, a spraying current of 420 A, a spraying power of 55 kW, and a spraying distance of 95 mm.

A cuboid test piece (20 mm×40 mm×5 mm) was created using the matrix with the composite coating above, and placed in a silicone oil tank of HYJH-3-4 piezoelectric polarization device tester. Voltage was applied across both side of the matrix for polarization, and the matrix was stood for 40 h, resulting in the matrix with the lead titanate coating. The polarization temperature was 120° C., the polarization duration was 20 min, and the intensity of the polarization electric field was 2.5 KV/mm.

Figure 29:
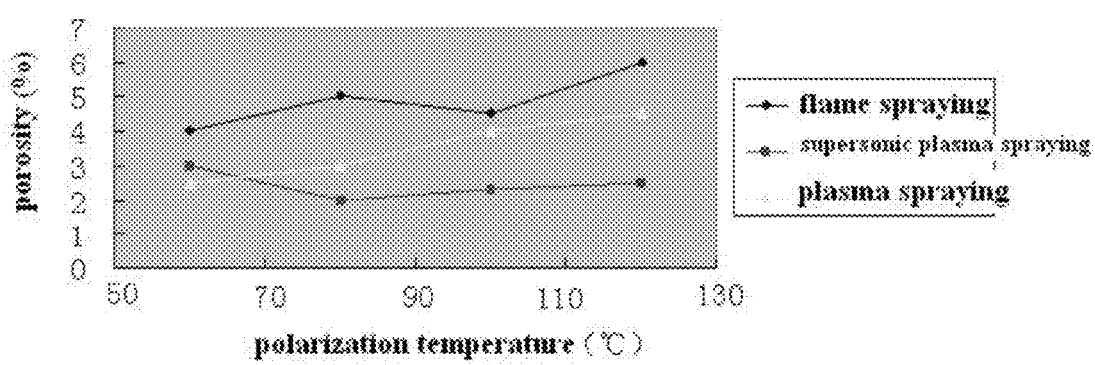
FIG. 29 is a graph showing the porosity of the coatings obtained by various spraying means in Examples 61-72 of the present invention as a function of the polarization temperature.

According to the method described above, the porosity of the lead titanate coating was measured. The results are shown in FIG. 29, which is a graph showing the porosity of the coatings obtained by various spraying methods in Examples 61-72 of the present invention as a function of polarization temperature. As can be seen from FIG. 29, the coating prepared according to Example 61 of the present invention has smaller porosity.

Examples 62-64

The matrices with the lead titanate coating were obtained according to the method in Example 61, except that the polarization temperature was changed to be 60° C., 80° C., and 100° C., respectively.

According to the method described above, the porosity of the lead titanate coating was measured. The results are shown in FIG. 29. As can be seen from FIG. 29, the coatings prepared according to Examples 61-64 of the present invention have smaller porosity.

Example 65

The matrix with the lead titanate coating was obtained according to the method in Example 61, except that the spraying method is changed to be plasma spraying.

According to the method described above, the porosity of the lead titanate coating was measured. The results are shown in FIG. 29. As can be seen from FIG. 29, the performance of the coating prepared by plasma spraying is worse than that prepared by supersonic plasma spraying.

Examples 66-68

The matrices with the lead titanate coating were obtained according to the method in Example 65, except that the polarization temperature was changed to be 60° C., 80° C., and 100° C., respectively.

According to the method described above, the porosity of the lead titanate coating was measured. The results are shown in FIG. 29. As can be seen from FIG. 29, the performance of the coatings prepared by plasma spraying was worse than those prepared by supersonic plasma spraying.

Example 69

The matrix with the lead titanate coating was obtained according to the method in Example 61, except that the spraying method is changed to be flame spraying.

According to the method described above, the porosity of the lead titanate coating was measured. The results are shown in FIG. 29. As can be seen from FIG. 29, the performance of the coating prepared by flame spraying is worse than that prepared by supersonic plasma spraying.

Examples 70-72

The matrices with the lead titanate coating were obtained according to the method in Example 69, except that the polarization temperature was changed to be 60° C., 80° C., and 100° C., respectively.

According to the method described above, the porosity of the lead titanate coating was measured. The results are shown in FIG. 29. As can be seen from FIG. 29, the performance of the coatings prepared by flame spraying is worse than those prepared by supersonic plasma spraying.

It can be seen from the examples above that, in the present invention, the piezoelectric material layer with the most sensitivity and the plasma spraying layer with the best performance can be obtained preferably by supersonic plasma spraying, and by optimal design of important process parameters, such as spraying voltage and spraying distance etc.

The above examples are demonstrated merely for helping to understand the methods and principal concepts of the present invention. It should be noted that several improvements and modifications can be made to the present invention by the person of ordinary skill in the art without departing from the principles of the present invention. These improvements and modifications should also be regarded as being within the scope of the claims of the present invention.

The invention claimed is:

1. A lead titanate coating, which is prepared by spraying a mixed powder on a surface of a matrix and subjecting it to polarization, wherein the mixed powder comprises $PbTiO_3$ powder, PbO powder and Al powder, wherein the mass ratio among the $PbTiO_3$ powder, the PbO powder and the Al powder is (5-8):(1-2):(1-3).

2. The lead titanate coating according to claim 1, wherein the particle size of the $PbTiO_3$ powder is in the range from 40 μm to 60 μm.

3. The lead titanate coating according to claim 2, wherein the particle size of the PbO powder is in the range from 40 μm to 70 μm.

4. The lead titanate coating according to claim 3, wherein the particle size of the Al powder is in the range from 30 μm to 40 μm.

5. The lead titanate coating according to claim 1, wherein the particle size of the PbTiO₃ powder is in the range from 40 μm to 60 μm.

6. The lead titanate coating according to claim 1, wherein the thickness of the lead titanate coating is in the range from 45 μm to 55 μm.

7. The lead titanate coating according to claim 1, wherein the thickness of the lead titanate coating is in the range from 45 μm to 55 μm.

8. The lead titanate coating according to claim 1, wherein the lead titanate coating further comprises a wear-resistant layer.

9. The lead titanate coating according to claim 1, wherein the lead titanate coating further comprises a wear-resistant layer.

10. The lead titanate coating according to claim 1, wherein the lead titanate coating further comprises a priming layer.

11. The lead titanate coating according to claim 1, wherein the lead titanate coating further comprises a priming layer.

12. The lead titanate coating according to claim 1, wherein the matrix is selected from gear, or cylinder and piston assembly.

13. A method for preparing a lead titanate coating, comprising the following steps:
(i) spraying a mixed powder on a surface of a matrix, and
(ii) subjecting the matrix to polarization to produce the lead titanate coating;
wherein the mixed powder comprises PbTiO₃ powder, PbO powder and Al powder, wherein the mass ratio among the PbTiO₃ powder, the PbO powder and the Al powder is (5-8):(1-2):(1-3).

14. The preparation method according to claim 13, wherein the spraying is supersonic plasma spraying.

15. A sensing system for a matrix surface failure, comprising:
(i) a sensing device; and
(ii) a signal analysis device for analyzing the signal output of the sensing device;
wherein the sensing device comprises a sensing unit comprising: (a) a lead titanate coating covering the surface of the matrix, which is used to perceive and convert the signal about the matrix surface failure; and (b) a first electrode arranged on the lead titanate coating, which is used to output the signal about the matrix surface failure;
and wherein the lead titanate coating is prepared by spraying a mixed powder on the surface of the matrix and subjecting it to polarization, wherein the mixed powder comprises PbTiO₃ powder, PbO powder and Al powder, wherein the mass ratio among the PbTiO₃ powder, the PbO powder and the Al powder is (5-8):(1-2):(1-3).

* * * * *